United States Patent [19]
Maier et al.

[11] Patent Number: 5,922,738
[45] Date of Patent: Jul. 13, 1999

[54] HETEROARYLPYRIDINE HERBICIDES

[75] Inventors: Thomas Maier; Stefan Scheiblich, both of Mainz; Helmut Siegfried Baltruschat, Schweppenhausen, all of Germany; Joseph Luke Pont, Langhorne, Pa.

[73] Assignee: American Cyanamid Company, Madison, N.J.

[21] Appl. No.: 08/889,773

[22] Filed: Jul. 8, 1997

Related U.S. Application Data

[60] Provisional application No. 60/023,317, Jul. 30, 1996.
[51] Int. Cl.[6] .......................... A01N 43/40; C07D 211/68; C07D 409/00; C07D 211/56
[52] U.S. Cl. .......................... 514/318; 514/326; 514/327; 546/193; 546/208; 546/212; 546/215; 546/216
[58] Field of Search .................................... 546/193, 208, 546/212, 215, 216; 514/318, 326, 327

[56] References Cited

FOREIGN PATENT DOCUMENTS

| 0 572 093 | 12/1993 | European Pat. Off. . |
|---|---|---|
| 0 692 474 | 1/1996 | European Pat. Off. . |
| 0 693 490 | 1/1996 | European Pat. Off. . |
| 0 694 538 | 1/1996 | European Pat. Off. . |
| WO94/22833 | 10/1994 | WIPO . |

OTHER PUBLICATIONS

U.S. application No. 08/889,863, Maier et al., filed Jul. 8, 1997, 546, 193

*Primary Examiner*—Mukund J. Shah
*Assistant Examiner*—Tamthom T. Ngo
*Attorney, Agent, or Firm*—Joseph M. Mazzarese

[57] ABSTRACT

The novel heteroaryloxypyridines of formula I:

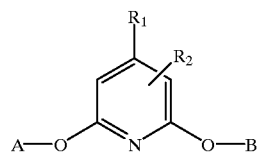

(A, B, $R_1$ and $R_2$ are defined in the specification) show excellent selective herbicidal activity.

The new compounds can be prepared according to known methods and can be used as herbicides in agriculture and related fields.

11 Claims, No Drawings

HETEROARYLPYRIDINE HERBICIDES

This application claims the benefit of U.S. Provisional Application No. 60/023,317, filed on Jul. 30, 1996.

BACKGROUND OF THE INVENTION

Selective herbicidal compounds play an important role in agriculture and related fields, because weeds cause considerable losses by reducing crop yields and lowering crop quality. Although numerous selective herbicides have been described, there is nevertheless a considerable interest in new compounds having superior or different herbicidal activity and/or selectivity.

Certain herbicidal compounds from the class of pyridine derivatives, and particularly 2,6-substituted pyridines, are known from EP0572093, EP0692474, EP0693490 and WO 94/22833.

The present invention describes novel, very effective, herbicidal 2,6-substituted pyridine derivatives having a superior selectivity compared to known compounds.

SUMMARY OF THE INVENTION

The present invention comprises novel heteroaryloxypyridines of formula I:

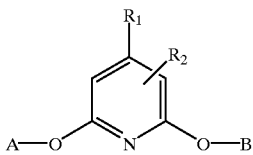

(I)

wherein

A represents one of the groups

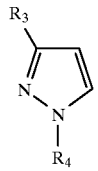

(A$_1$)

or

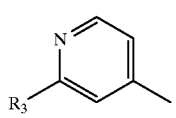

(A$_2$)

B represents one of the groups A$_1$ or A$_2$ or one of the groups

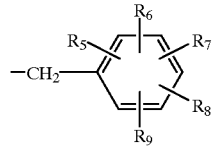

(B$_1$)

or

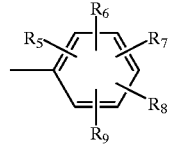

(B$_2$)

or

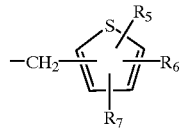

(B$_3$)

R$_1$ represents a cyano or NH(C$_{1-4}$ alkyl) group and may further represent a hydrogen or halogen atom, a C$_{1-4}$ alkyl, a C$_{1-4}$ haloalkyl, a C$_{1-4}$ alkoxy or a C$_{1-4}$ alkylthio group, if at least one of the following conditions is fulfilled:
  (a) at least one of the groups R$_3$ contained in A and/or B (i.e., if B represents A$_1$ or A$_2$) is C$_{1-4}$ haloalkoxy or C$_{1-4}$ haloalkylthio;
  (b) B has the meaning B$_3$;
  (c) B has the meaning B$_1$ or B$_2$ and at least one of the groups R$_{5-7}$ represent C$_{1-4}$ haloalkoxy or C$_{1-4}$ haloalkylthio;

R$_2$ represents a hydrogen or fluorine atom;

R$_3$ represents a halogen atom, a cyano, C$_{1-4}$ alkyl, C$_{1-4}$ haloalkyl, C$_{1-4}$ haloalkoxy or C$_{1-4}$ haloalkylthio group;

R$_4$ represents a C$_{1-4}$ alkyl group;

R$_5$, R$_6$, R$_7$ independently represent a hydrogen or halogen atom or a C$_{1-4}$ alkyl, C$_{1-4}$ haloalkyl, C$_{1-4}$ alkoxy, C$_{1-4}$ haloalkoxy, C$_{1-4}$ alkylthio, C$_{1-4}$ haloalkylthio, cyano or nitro group; and R$_8$, R$_9$ independently represent a hydrogen or halogen atom or a C$_{1-4}$ alkyl group.

This invention also comprises methods for combatting undesired plant growth using compounds of formula I.

It is an object of the present invention to provide novel herbicidal compounds having superior herbicidal properties.

It is another object of the invention to provide methods for controlling undesired plant growth by contacting said plants with a herbicidally effective amount of the new compounds.

It is another object of the invention to provide selective herbicidal compositions containing the new compounds as active ingredient together with carrier material and/or additives.

These and other objects and advantages of the invention will be apparent from the detailed description set forth herein below, and from the appended claims.

DETAILED DESCRIPTION OF THE INVENTION

One important aspect of the present invention is novel compounds having excellent herbicidal activity combined with improved selectivity and partly enhanced soil degradation, which comprise heteroaryloxypyridines of formula I:

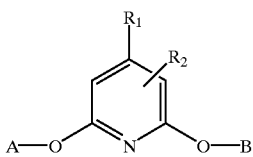

(I)

wherein A, B, $R_1$ and $R_2$ are as defined above.

In the terminology used throughout this disclosure, groups comprising or being a haloalkyl moiety may contain one or more halogen atoms, e.g., trifluoromethyl, difluoromethoxy, trifluoromethoxy, 2,2,2-trifluoroethoxy, and the like. Alkyl groups and the alkyl moieties of any other groups comprising three or more carbon atoms may be straight or branched.

The term "halogen" means fluorine, chlorine, bromine and iodine atoms, preferably fluorine, chlorine and bromine atoms and particularly fluorine and chlorine atoms.

Preferred compounds according to the invention include those wherein:

$R_3$ is chlorine, $C_{1-4}$ fluoroalkyl, $C_{1-4}$ fluoroalkoxy or $C_{1-4}$ fluoroalkylthio;

$R_4$ is methyl or ethyl; and, when B is $B_1$ or $B_2$ at least two of the substituents $R_5$ to $R_9$ are hydrogen atoms and when B is $B_3$ at least $R_7$ is a hydrogen atom, and the remaining substituents contained in $B_1$, $B_2$ or $B_3$ independently represent a hydrogen, chlorine or fluorine atom or a methyl, trifluoromethyl or $C_{1-2}$ -fluoroalkoxy group.

Particularly preferred are those compounds, wherein $R_3$ is $CF_3$, $C_2F_5$, $CHF_2O$ or $CF_3CH_2O$; $R_4$ is methyl; and B is a group of formula $B_1'$:

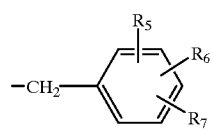

($B_1'$)

wherein $R_5$, $R_6$ and $R_7$ are independently hydrogen or fluorine atoms and $R_5$ can further represent a methyl group;

or a group of formula $B_2'$:

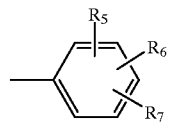

($B_2'$)

wherein $R_5$, $R_6$ and $R_7$ independently represent a hydrogen, fluorine or chlorine atom and $R_5$ can further represent a trifluoromethyl, an $OCHF_2$
or an $OCH_2CF_3$ group;

or a group of formula $B_3'$:

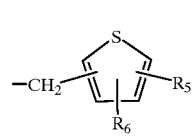

($B_3'$)

wherein $R_5$ and $R_6$ independently are hydrogen, fluorine or chlorine atoms and $R_5$ can further represent a methyl or trifluormethyl group. If $R_5$ is a methyl group, it is preferably in a vicinal position to the $CH_2$ group.

Especially preferred are the compounds of the group comprising 2,6-bis(1-methyl-3-trifluoromethylpyrazol-5-yloxy)-4-methylaminopyridine;
2,6-bis(1-methyl-3-trifluoromethylpyrazol-5-yloxy)-4-cyanopyridine;
2,6-bis(2-difluoromethoxy-4-pyridyloxy)-4-methylpyridine;
6-(3,4-difluorobenzyloxy)-2-(1-methyl-3-trifluormethylpyrazol-5-yloxy)-4-cyanopyridine;
6-(4-fluorobenzyloxy)-2-(1-methyl-3-trifluoromethylpyrazol-5-yloxy)-4-cyanopyridine;
2-(1-methyl-3-trifluoromethylpyrazol-5-yloxy)-6-(thien-2-ylmethoxy)-4-methylpyridine;
2-(1-methyl-3-trifluoromethylpyrazol-5-yloxy)-6-(5-chlorothien-2-ylmethoxy)-4-methylpyridine;
2-(1-methyl-3-trifluoromethylpyrazol-5-yloxy)-6-(5-trifluoromethythien-2-ylmethoxy)-4-methylpyridine;
2-(1-methyl-3-trifluoromethylpyrazol-5-yloxy)-6-(5-fluorothien-2-ylmethoxy)-4-methylpyridine;
2-(1-methyl-3-trifluoromethylpyrazol-5-yloxy)-6-(thien-3-ylmethoxy)-4-methylpyridine;
2-(1-methyl-3-trifluoromethylpyrazol-5-yloxy)-6-(5-fluorothien-2-ylmethoxy)-4-methoxypyridine;
2-(2-trifluoromethylpyrid-4-yloxy)-6-(thien-2-ylmethoxy)-4-methylpyridine;
2-(2-trifluoromethylpyrid-4-yloxy)-6-(thien-3-ylmethoxy)-4-methylpyridine;
2-(2-difluoromethoxypyrid-4-yloxy)-6-(thien-2-ylmethoxy)-4-methylpyridine;
2-(2-difluoromethoxypyrid-4-yloxy)-6-(thien-3-ylmethoxy)-4-methylpyridine; and
2-(2-difluoromethoxypyrid-4-yloxy)-6-(4-fluorobenzyloxy)-4-methylpyridine.

The pyridine compounds of the present invention can be prepared according to known methods, for example as follows:

(A) A compound of formula II:

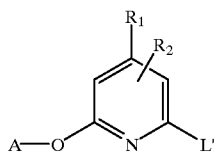

(II)

wherein A, R₁ and R₂ are defined as in relation to formula I and L' is a suitable leaving group (such as alkyl- or arylsulfonyl, aryl- or alkylsulfonyloxy, nitro or halogen, particularly a fluorine, chlorine or bromine atom), is reacted with about one equivalent of a metal salt of a compound of formula III:

 (III)

wherein B is defined as in relation to formula I, under basic conditions, or in the presence of a basic compound, e.g., an alkali hydroxide, alkoxide, carbonate, or triethylamine.

The reaction is carried out at elevated temperature in a polar solvent, such as N-methylpyrrolidone (NMP), dimethylsulfoxide (DMF) or sulfolane. If the compound of formula III is used as a salt, it may be an alkali salt. The presence of a copper salt may be advantageous.

(B) A compound of formula IV:

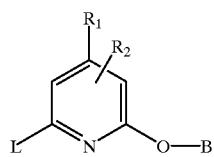

(IV)

wherein B, R₁ and R₂ are defined as in relation to formula I and L is a suitable leaving group (such as alkyl- or arylsulfonyl, aryl- or alkylsulfonyloxy, nitro or halogen, particularly a fluorine, chlorine or bromine atom), is reacted with a compound of formula V:

 (V)

wherein A is defined as in relation to formula I, or a tautomer thereof. The reaction can be carried out in a similar manner and under similar conditions as reaction 1 above, i.e., in the presence of a basic compound or with V in the form of a metal salt and/or in the presence of a copper catalyst. About one equivalent or a slight excess of V is used.

(C) For the preparation of compounds wherein B represents $B_1$, $B_2$ or $B_3$, a compound of formula VI:

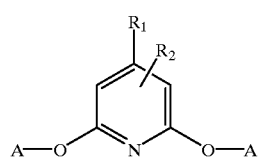

(VI)

wherein A, R₁ and R₂ are defined as in relation to formula I, is reacted with about one equivalent of a compound of formula III, e.g., in form of its metal salt, in a polar solvent at elevated temperature. The reaction is carried out similarly to process 1 above.

(D) A compound of formula VII:

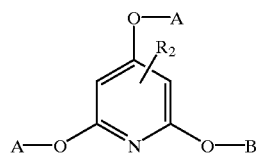

(VII)

wherein A, B and R₂ are defined as in relation to formula I, is reacted with a compound of formula VIII:

 (VIII)

wherein R₁ is defined as above, or a metal salt thereof, under basic conditions.

(E) For the preparation of compounds of formula I, wherein R₁ denotes a halogen atom or a cyano group, an amino compound of formula IX:

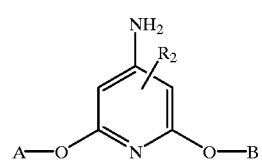

(IX)

can be diazotized and the diazonium group can be replaced by halogen or cyano by reacting the diazonium salt with a suitable halogenide or cyanide.

The routes for the preparation of the compounds of formulae II, IV, VI and VII can be as follows:

The compound of formula X:

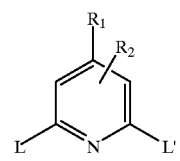

(X)

(L, L', R₁ and R₂ are defined as hereinbefore) can be reacted with one equivalent of V (as metal salt or in the presence of a base) to give II. If at least two equivalents of V are being used, the main product is VI, whereas the reaction with one equivalent of III leads mainly to IV.

Compounds of formula XI:

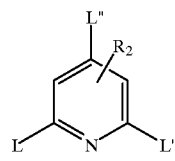

(XI)

(L, L', L" and R₂ are defined as above) can be reacted with a suitable amount of V to give

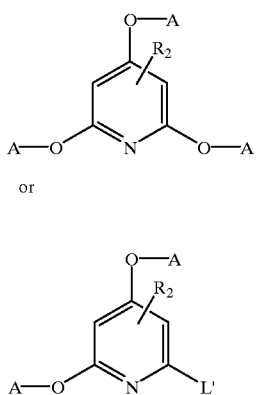

(XII)

or (XIII)

The 4-O—A group can be replaced by $R_1$ to give VI or II, or can be replaced by an amino group which may be converted to halogen or cyano via the diazonium salt. Compounds of formula XIII can be further reacted with III to give VII. Intermediates of formula III containing the group $B_3$ can be prepared by reduction of corresponding carboxylic acid derivatives.

Starting materials for which preparations are not described herein can be prepared according to known methods.

The present invention also extends to herbicidal compositions and to a method of preparing herbicidal compositions containing at least one new compound according to the invention which method comprises blending a compound of formula I with at least one carrier.

Preferably there are at least two carriers or additives present in a composition according to the invention, at least one of which is a surface-active agent.

A carrier in a composition according to the invention is any material with which the active ingredient is formulated to facilitate application to the locus to be treated (which locus may be as appropriate, a plant, seed or soil), or to facilitate storage, transport or handling. A carrier may be a solid or a liquid, including a material which is normally gaseous but which has been compressed to form a liquid, and any of the carriers normally used in formulating herbicidal compositions may be used. Preferably compositions according to the invention contain 0.5 to 95% by weight of active ingredient.

Suitable solid carriers include natural and synthetic clays and silicates, for example natural silicates such as diatomaceous earths; magnesium silicates, for example talcs; magnesium aluminium silicates, for example attapulgites and vermiculites; aluminium silicates, for example kaolinites, montmorillonites and micas; calcium carbonate; calcium sulphate; ammonium sulphate; synthetic hydrated silicon oxides and synthetic calcium or aluminium silicates; elements, for example carbon and sulphur; natural and synthetic resins, for example coumaron resins, polyvinyl chloride, and styrene polymers and copolymers; solid polychlorophenols; bitumen; waxes; solid fertilisers, for example superphosphates.

Suitable liquid carriers include water; alcohols, for example isopropanol and glycols; ketones, for example acetone, methyl ethyl ketone, methyl isobutyl ketone and cyclohexanone; ethers; aromatic or araliphatic hydrocarbons, for example benzene, toluene and xylene; petroleum fractions, for example kerosene and light mineral oils; chlorinated hydrocarbons, for example carbon tetrachloride, perchloroethylene and trichloroethane. Mixtures of such liquids are often suitable.

Agricultural compositions are often formulated and transported in a concentrated form, which is subsequently diluted by the user before application. The presence of small amounts of a carrier which is a surface-active agent facilitates this process of dilution. Thus, preferably at least one carrier in a composition according to the invention is a surface active agent. For example, the composition may contain in addition to the active ingredient at least two further components, at least one of which is a surface-active agent.

A surface-active agent may be an emulsifying agent, a dispersing agent or a wetting agent; it may be non-ionic or ionic. Examples of suitable surface-active agents include the sodium or calcium salts of polyacrylic acids and lignin sulphonic acids; the condensation products of fatty acids or aliphatic amines or amides (containing at least 12 carbon atoms in the molecule) with ethylene oxide and/or propylene oxide; fatty acid esters of glycerol, sorbitol, sucrose or pentaerythrol; condensates of these with ethylene oxide and/or propylene oxide; condensation products of fatty alcohol or alkyl phenols, for example p-octylphenol or p-octylcresol, with ethylene oxide and/or propylene oxide; sulphates or sulphonates of these condensation products; alkali or earth alkali metal salts, preferably sodium salts, or sulphuric or sulphonic acd esters containing at least 10 carbon atoms in the molecule, for example sodium lauryl sulphate, sodium secondary alkyl sulphates, sodium salts of sulphonated castor oil, and sodium alkylaryl sulphonates such as dodecylbenzene sulphonate; and polymers of ethylene oxide and copolymers of ethylene oxide and propylene oxide.

The herbicidal composition of the invention may also contain other active ingredients, for example, compounds possessing insecticidal or fungicidal properties, or other herbicides. The compositions may be suspensions, solutions, emulsion or suspension concentrates, wettable powders, granulates and the like.

A typical example of a formulation containing a compound according to the invention is 100 g of active ingredient (compound of formula I), 30 g of dispersing agent, 3 g of antifoaming agent, 2 g of structure agent, 50 g of anti-freezing agent, 0.5 g of a biocidal agent and enough water to make 1000 ml. Prior to use, it is diluted with water to give the desired concentration of active ingredient.

A further aspect of the invention is to provide methods for controlling undesired plant growth by contacting said plants with a herbicidally effective amount of the new compounds. The compounds of formula I can be used for pre- and post-emergence application. The active compounds or the compositions according to the invention can be applied directly to the plants or to the locus in need of treatment. The amount of active compound needed per hectare depends to some extent on the compound and the formulation used, of the kind of the undesired plants and of the climatic conditions. As a rule, the effective amount of active compound is 0.005 to 1, preferably 0.01 to 0.5 kg/ha.

For a more clear understanding of the invention, specific examples are set forth below. These examples are merely illustrations and are not to be understood as limiting the scope and underlying principles of the invention in any way. Various modifications of the invention in addition to those shown and described herein will become apparent to those skilled in the art from the following examples and foregoing description. Such modifications are also intended to fall within the scope of the appended claims.

EXAMPLE 1

(a) 2,4,6-Tris(1-methyl-3-trifluoromethylpyrazol-5-yloxy) pyridine

A stirred mixture of 2,4,6-trifluoropyridine (4.8 g, 36 mmol), 5-hydroxy-1-methyl-3-trifluoromethylpyrazole (19.8 g, 119 mmol) and potassium carbonate (18.1 g, 131 mmol) in anhydrous sulfolane (25 ml) is heated to 80° C. over a period of 3 days.

After cooling, the mixture is diluted with pentane/ethyl acetate (1/1 ratio by volume) and filtered through a bed of silica gel. The filtrate is washed 10 times with water and the organic layer is dried over magnesium sulfate. After removal of the solvents, the residue is washed with isopropyl ether. One obtains 19.1 g (93% yield) colorless crystals of melting point 130° C.

(b) 2.6-Bis(1-methyl-3-trifluoromethylpyrazol-5-yloxy)-4-methylaminopyridine 2,4,6-Tris(1-methyl-3-trifluoromethylpyrazol-5-yloxy) pyridine (1 g, 1.75 mmol) (from Example 1(a)) is dissolved in a solution of 33% methylamine in ethanol. The mixture is stirred at ambient temperature overnight. Now the solvent is removed in vacuo and the residue is coevaporated with toluene and methanol. The crude product is purified by a flash silica gel column chromatography using pentane/ethyl acetate in a ratio volume of 7/3 and at least 1/1. 0.4 g (52% yield) of the title compound were obtained as a white solid of melting point 118° C.

EXAMPLE 2

4-Cyano-2.6-bis(1-methyl-3-trifluoromethylpyrazol-5-yloxy)pyridine

A mixture of 2,6-dichloro-4-cyanopyridine (3.5 g, 20 mmol), 5-hydroxy-1-methyl-3-trifluoromethylpyrazole (7.4 g, 44 mmol), potassium carbonate (6.2 g, 44 mmol) and sulfolane (10 ml) is heated to 90° C. overnight. After cooling, the mixture is diluted with ethyl acetate/pentane (2/1 by volume) and filtered through a bed of silica gel. The filtrate is washed 6 times with water. After drying and evaporation of the organic layer, the residue is purified by column chromatography (silica gel: pentane/ethyl acetate 8/2). One obtains 5.8 g (67% yield) colorless crystals of melting point 140° C.

EXAMPLE 3

Preparation of 2,6-Bis(2-difluoromethoxy-4-pyridyloxy)-4-methylpyridine 0.56 g 2-Bromo-6-fluoro-4-methylpyridine are dissolved in 30 ml dry NMP 1.0 g 2-difluoromethoxy-4-hydroxypyridine and 2.57 g potassium carbonate are added and the mixture is stirred at 100° C. for 15 hrs, then another 18 hrs at 150° C. The mixture is diluted with ethyl acetate, washed with water and chromatographed to give 0.65 g of the title compound (m.p. 60–65° C.).

EXAMPLE 4

4-Cyano-6-(2,4-difluorobenzyloxy)-2-(1-methyl-3-trifluoromethylpyrazol-5-yloxy)pyridine Sodium hydride (0.1 g, 60%, 2.5 mmol) is added to a solution of 2,4-difluorobenzyl alcohol (0.28 ml, 2.5 mmol) in sulfolane (5 ml) at 50° C. After 1 hour at 50° C., 4-cyano-2,6-bis(1-methyl-3-trifluoromethylpyrazol-5-yloxy)pyridine (1 g, 2.3 mmol) (from Example 2) is added to the reaction mixture. The mixture is heated to 90° C. overnight. After cooling, the reaction mixture is diluted with pentane/ethyl acetate (by volume ration 1/1) and filtered through a bed of silica gel. The filtrate is washed 6 times with water. The organic layer is dried with anhydrous magnesium sulfate, filtered and evaporated in vacuo. Purification by flash chromatography (silica gel: pentane/ethyl acetate 8/2 v/v) and washing of the product with diisopropyl ether yields the title compound (0.2 g, 21% yield) of melting point 109° C.

EXAMPLE 5

Following procedures analogous to Examples 1–4, further compounds of the invention can be prepared. Details are given below in Tables 1 to 3.

TABLE 1

(Ia)

A—O—[pyridine ring with $R_1$]—O—B

| Comp No. | $R_1$ | A | B | m.p. [° C.] |
|---|---|---|---|---|
| 1 | Me | 2-difluoromethoxy-4-pyridyl | 4-fluorobenzyl | 57–63 |
| 2 | Me | 1-CH$_3$-3-CF$_3$-pyrazol-5-yl | 2-difluoromethoxy-4-pyridyl | |
| 3 | Me | 2-(2,2,2-trifluoroethoxy)-4-pyridyl | 2-(2,2,2-trifluoroethoxy)-4-pyridyl | |
| 4 | Me | 1-CH$_3$-3-CF$_3$-pyrazol-5-yl | 3-(difluoromethoxy)phenyl | |
| 5 | Me | 1-CH$_3$-3-CF$_3$-pyrazol-5-yl | 2-(2,2,2-trifluoroethoxy)-4-pyridyl | |
| 6 | Me | 2-(2,2,2-trifluoroethoxy)-4-pyridyl | 4-fluorobenzyl | 48–50 |
| 7 | CN | 1-CH$_3$-3-CF$_3$-pyrazol-5-yl | 4-fluorobenzyl | 98 |
| 8 | CN | 1-CH$_3$-3-CF$_3$-pyrazol-5-yl | 3,4-difluorobenzyl | 94 |
| 9 | Me | 1-CH$_3$-3-CF$_3$-pyrazol-5-yl | 3-(trifuoromethoxy)phenyl | 40 |
| 10 | Me | 2-(difluoromethoxy)-4-pyridyl | 3-fluorobenzyl | oil |
| 11 | Me | 2-(2,2,2-trifluoroethoxy)-4-pyridyl | 3-fluorobenzyl | oil |
| 12 | Me | 2-(difluoromethoxy)-4-pyridyl | 2-methylbenzyl | oil |
| 13 | Me | 2-(2,2,2-trifluoroethoxy)-4-pyridyl | 2-methylbenzyl | oil |
| 14 | Me | 2-(difluoromethoxy)-4-pyridyl | benzyl | oil |
| 15 | Me | 2-(2,2,2-trifluoroethoxy)-4- | benzyl | oil |

TABLE 1-continued (Ia)

Structure: R1-substituted pyridine with A—O and O—B substituents

| Comp No. | R1 | A | B | m.p. [° C.] |
|---|---|---|---|---|
| | | pyridyl | | |

TABLE 2

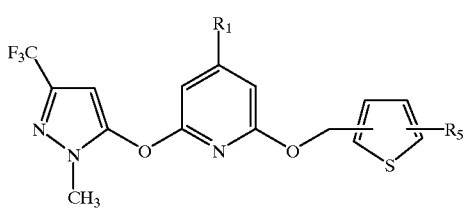

(Ib)

| Compound No. | R1 | R5 | thiophene connected at position | m.p. [° C.] |
|---|---|---|---|---|
| 1 | Me | H | 2 | oil |
| 2 | Me | 5-Cl | 2 | 60 |
| 3 | Me | H | 3 | oil |
| 4 | MeO | 5-CF3 | 2 | |
| 5 | MeO | 5-CF3 | 3 | |
| 6 | MeO | 5-F | 2 | |
| 7 | MeO | 5-F | 3 | |
| 8 | Me | 3-F | 2 | |
| 9 | Me | 4-F | 2 | |
| 10 | Me | 5-F | 2 | |
| 11 | Me | 2-F | 3 | |
| 12 | Me | 5-F | 3 | |
| 13 | MeO | H | 2 | |
| 14 | MeO | H | 3 | |
| 15 | CN | H | 2 | |
| 16 | CN | H | 3 | |
| 17 | CN | 3-Me | 2 | |
| 18 | MeO | 3-Me | 2 | |
| 19 | Me | 3-Me | 2 | oil |

TABLE 3

(Ic)

| Compound No. | R1 | R5 | R3 | thiophene connected at position | m.p. [° C.] |
|---|---|---|---|---|---|
| 1 | Me | H | CF3 | 2 | oil |
| 2 | Me | 5-Cl | CF3 | 2 | |
| 3 | Me | H | CF3 | 3 | |
| 4 | MeO | H | CF3 | 2 | |
| 5 | MeO | 5-Cl | CF3 | 2 | |
| 6 | MeO | H | CF3 | 3 | |

TABLE 3-continued (Ic)

| Compound No. | R1 | R5 | R3 | thiophene connected at position | m.p. [° C.] |
|---|---|---|---|---|---|
| 7 | CN | H | CF3 | 2 | |
| 8 | CN | H | CF3 | 3 | |
| 9 | Me | H | CHF2O | 2 | oil |
| 10 | Me | 5-Cl | CHF2O | 2 | |
| 11 | Me | H | CHF2O | 3 | |
| 12 | MeO | H | CHF2O | 2 | |
| 13 | MeO | 5-Cl | CHF2O | 2 | |
| 14 | MeO | H | CHF2O | 3 | |
| 15 | CN | H | CHF2O | 2 | |
| 16 | CN | H | CHF2O | 3 | |

EXAMPLE 6

Biological Evaluation

Pre-emergence Herbicidal Evaluation of Test Compounds

The pre-emergence herbicidal activity of the compounds of the present invention is exemplified by the following test in which the seeds of a variety of monocotyledonous and dicotyledonous plants are seperately mixed with potting soil and planted on top of approximately one inch of soil in separate pots. After planting, the pots are sprayed with an aqueous acetone solution containing test compound in sufficient quantity to provide the equivalent of about 0.025 to 0.4 kg per hectare of test compound per pot. The treated pots are then placed on greenhouse benches, watered and cared for in accordance with conventional greenhouse procedures.

From 2 to 4 weeks after treatment, the tests are terminated and each pot is examined and rated according to the rating system set forth below.

| Rating System Growth | % Difference in from the control |
|---|---|
| 0 - No effect | 0 |
| 1 - Trace effect | 1–5 |
| 2 - Slight effect | 6–15 |
| 3 - Moderate effect | 16–29 |
| 4 - Injury | 30–44 |
| 5 - Definite injury | 45–64 |
| 6 - Herbicidal effect | 65–79 |
| 7 - Good herbicidal effect | 80–90 |
| 8 - Approaching complete kill | 91–99 |
| 9 - Complete kill | 100 |

| Plant Species Used | | |
|---|---|---|
| A = TRZAW | Triticum aestivum | winter wheat |
| B = HORVW | Hordeum vulgare | winter barley |
| C = ZEAMX | Zea mays | maize |
| D = ORYSA | Oryza sativum | rice |
| E = GLYMA | Glycine max | soyabeans |
| F = ALOMY | Alopecurus myosuroides | blackgrass |
| G = SETVI | Setaria viridis | green foxtail |
| H = ABUTH | Abutilon theophrasti | velvetleaf |
| I = GALAP | Galium aparine | cleaver |

| | | | |
|---|---|---|---|
| J = IPOHE | Ipomoea hederacea | morning glory |
| K = LAMPU | Lamium purpureum | purple adnette |
| L = MATIN | Matricaria inodora | mayweed |
| M = PAPRH | Papaver rhoeas | poppy |
| N = VERPE | Veronica persica | speedwell |
| O = STEME | Stellaria media | chickweed |
| P = AMBEL | Ambrosia artemisiifolia | ragweed |
| Q = CHEAL | Chenopodium album | lambsquarter |

(First column: BAYER-Codes and corresponding letters used in the tables).

The herbicidal proficiency of the active ingredients of the present invention is evident from the test results which are recorded in Table A–D below.

TABLE A

Crop selectivity and weed control in pre-emergence application
CROP AND WEED SPECIES

| compound | dose [kg/ha] | A | C | E | F | G | H | J | K | L | M | N | O |
|---|---|---|---|---|---|---|---|---|---|---|---|---|---|
| Tab. 2/no. 1 | 0.400 | 5 | 5 | 6 | 9 | 9 | 9 | 9 | 9 | 9 | 9 | 9 | 9 |
|  | 0.100 | 5 | 4 | 6 | 9 | 9 | 9 | 9 | 9 | 8 | 9 | 9 | 9 |
|  | 0.025 | 4 | 2 | 4 | 8 | 8 | 6 | 8 | 9 | 8 | 9 | 8 | 9 |
| Tab. 2/no. 2 | 0.400 | 4 | 4 | 4 | 9 | 9 | 9 | 8 | 9 | 9 | 9 | 9 | 9 |
|  | 0.100 | 3 | 3 | 2 | 9 | 9 | 7 | 5 | 9 | 9 | 9 | 9 | 9 |
|  | 0.025 | 1 | 2 | 2 | 7 | 7 | 4 | 4 | 8 | 8 | 9 | 9 | 9 |
| Standard 1* | 0.400 | 5 | 6 | 6 | 9 | 9 | 9 | 9 | 9 | 9 | 9 | 9 |  |
|  | 0.100 | 4 | 5 | 5 | 9 | 9 | 9 | 7 | 8 | 9 | 9 | 9 | 9 |
|  | 0.025 | 2 | 4 | 3 | 4 | 4 | 7 | 6 | 8 | 9 | 9 | 9 | 9 |

*standard 1: 4-methyl-2,6-bis(1-methyl-3-trifluoromethylpyrazol-5-yloxy)pyridine The compounds of the invention show clearly better selectivity in maize than standard 1. At a dose of 25 g/ha, the compounds of the invention exhibit good selectivity in maize, while the same dose of the standard leads to unacceptable levels of phytotoxicity in maize. Furthermore, the compound of Table 2/no. 1 showed superior activity on Setaria and Ipomoea over the standard. The compound of Table 2/no.2 also has superior selectivity in soybeans compared to the standard.

TABLE B

Crop selectivity and weed control in pre-emergence application
CROP AND WEED SPECIES

| Compound | dose [kg/ha] | B | C | E | G | H | P | J | Q | L | O |
|---|---|---|---|---|---|---|---|---|---|---|---|
| Table 1/no. 7 | 0.100 | 4 | 2 | 3 | 9 | 4 | 8 | 4 | 9 | 8 | 8 |
|  | 0.025 | 2 | 2 | 2 | 8 | 3 | 7 | 2 | 8 | 8 | 6 |
|  | 0.0125 | 1 | 0 | 2 | 5 | 2 | 4 | 1 | 7 | 5 | 3 |
| Table 1/no. 8 | 0.100 | 4 | 2 | 4 | 9 | 7 | 9 | 6 | 8 | 9 | 9 |
|  | 0.025 | 3 | 1 | 2 | 9 | 4 | 9 | 3 | 8 | 9 | 8 |
|  | 0.0125 | 1 | 1 | 2 | 7 | 4 | 9 | 3 | 7 | 9 | 7 |
| standard 2* | 0.100 | 4 | 4 | 4 | 9 | 7 | 9 | 7 | 8 | 9 | 9 |
|  | 0.025 | 3 | 2 | 4 | 9 | 7 | 8 | 7 | 8 | 9 | 9 |
|  | 0.0125 | 3 | 1 | 2 | 9 | 4 | 7 | 4 | 8 | 8 | 7 |

*standard 2: 4-methyl-2-(1-methyl-3-trifluormethylpyrazol-5-yloxy)-6-benzyloxypyridine The compounds of the present invention, Table 1/no.8 and Table 1/no. 7, have good selectivity in maize up to the highest dose of 100 g/ha and in soybeans at a dose of 25 g/ha, while standard 2 is less selective.

TABLE C

Crop selectivity and weed control in pre-emergence application
CROP AND WEED SPECIES

| Compound | kg/ka | A | C | G | F | J | K | L | M | N | O |
|---|---|---|---|---|---|---|---|---|---|---|---|
| Example 3 | 0.400 | 2 | 3 | 8 | 8 | 9 | 8 | 9 | 9 | 9 | 9 |
|  | 0.100 | 2 | 2 | 8 | 7 | 8 | 8 | 8 | 9 | 9 | 9 |
|  | 0.025 | 0 | 1 | 6 | 5 | 4 | 8 | 7 | 9 | 9 | 7 |
|  | 0.0125 | 0 | 1 | 5 | 4 | 2 | 4 | 6 | 9 | 7 | 2 |
| Standard 2* | 0.400 | 8 | 6 | 9 | 8 | 9 | 9 | 9 | 9 | 9 | 9 |
|  | 0.100 | 4 | 4 | 9 | 8 | 9 | 9 | 9 | 9 | 9 | 9 |
|  | 0.025 | 3 | 3 | 9 | 8 | 8 | 8 | 9 | 9 | 9 | 8 |
|  | 0.0125 | 3 | 2 | 8 | 8 | 8 | 8 | 9 | 9 | 9 | 8 |

*standard 2: 4-methyl-2-(1-methyl-3-trifluormethylpyrazol-5-yloxy)-6-benzyloxypyridine The compound of the invention is clearly more selective in wheat and maize than the standard. Example 3 has good selectivity in wheat up to the highest dose of 400 g/ha and in maize up to 100 g/ha, while the standard is much less selective. At crop selective doses, the compound of the invention has excellent activity on grasses such as Alopecurus and Setaria and on broad leaved weeds.

Post-emergence Herbicidal Evaluation of Test Compounds

The post-emergence herbicidal activity of the compounds of the present invention is demonstrated by the following test, wherein monocotyledonous and dicotyledonous plants are treated with formulations prepared from solutions of the test compounds in acetone containing 0.4% by weight of an alkylphenol/ethylene oxide condensate available under the trade mark TRITON X-155. These acetone solutions are diluted with water and the resulting formulations applied at dosage levels equivalent to about 0.025 to 0.4 kg per hectare of test compound per pot. After spraying, the plants are placed on greenhouse benches and are cared for in the usual manner, commensurate with conventional greenhouse practices. From 2 to 4 weeks after treatment, the seedling plants are examined and rated according to the rating system provided above. A rating 0 indicates growth as untreated control, a rating 9 indicates death. The results of the test are set out in Table D below.

The compounds of the invention show good activity on monocotyledonous and dicotyledonous weeds and low phytotoxicity in maize down to the lowest dose of 25 g/ha. At this dose, the compound of Table 2/no. 2 is also well tolerated by barley and wheat and active on key species in cereals such as Galium aparine, Veronica hederaefolia or Papaver rhoeas.

TABLE D

Crop selectivity and weed control in post-emergence application
CROP AND WEED SPECIES

| compound | dose [kg/ha] | A | B | C | E | F | H | J | K | L | M | N | O | I |
|---|---|---|---|---|---|---|---|---|---|---|---|---|---|---|
| Table 2/no. 1 | 0.400 | 4 | 5 | 5 | 8 | 7 | 9 | 6 | 8 | 6 | 8 | 8 | 8 | 6 |
| | 0.100 | 3 | 4 | 4 | 6 | 7 | 9 | 4 | 8 | 5 | 5 | 8 | 8 | 5 |
| | 0.025 | 3 | 3 | 2 | 6 | 5 | 9 | 3 | 8 | 4 | 4 | 8 | 8 | 5 |
| Table 2/no. 3 | 0.400 | 4 | 5 | 5 | 8 | 7 | 9 | 7 | 7 | 7 | 9 | 9 | 7 | 6 |
| | 0.100 | 3 | 4 | 4 | 7 | 6 | 9 | 6 | 6 | 5 | 9 | 9 | 5 | 5 |
| | 0.025 | 3 | 3 | 2 | 7 | 5 | 9 | 6 | 4 | 5 | 8 | 8 | 5 | 4 |
| Table 2/no. 2 | 0.400 | 3 | 3 | 5 | 8 | 8 | 7 | 9 | 8 | 9 | 9 | 9 | 7 | 9 |
| | 0.100 | 3 | 3 | 3 | 5 | 8 | 6 | 9 | 8 | 6 | 9 | 9 | 5 | 8 |
| | 0.025 | 2 | 2 | 2 | 5 | 5 | 4 | 8 | 5 | 5 | 9 | 8 | 5 | 8 |

What is claimed is:

1. A herbicidal compound comprising a heteroaryloxypyridine of formula I:

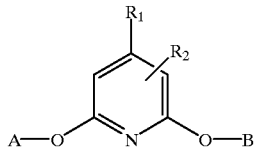
(I)

wherein

A represents one of the groups $A_1$ or $A_2$

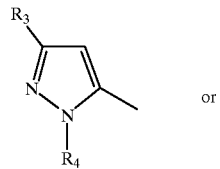
(A$_1$)

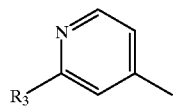
(A$_2$)

B represents independently one of the groups $A_1$ or $A_2$ or one of the groups $B_1$, or $B_2$

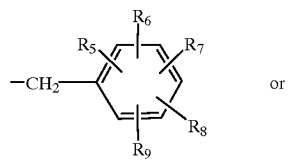
(B$_1$)

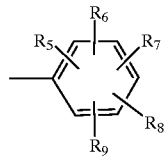
(B$_2$)

$R_1$ represents a cyano or NH($C_{1-4}$ alkyl)group and may further represent a hydrogen or halogen atom, a $C_{1-4}$ alkyl, a $C_{1-4}$ haloalkyl, or a $C_{1-4}$ alkylthio group, if at least one of the groups $R_3$, $R_5$, $R_6$ and $R_7$ represents a $C_{1-4}$ haloalkoxy or $C_{1-4}$ haloalkylthio group;

$R_2$ represents a hydrogen or fluorine atom;

$R_3$ represents a halogen atom, a cyano, $C_{1-4}$ alkyl, $C_{1-4}$ haloalkyl, $C_{1-4}$ haloalkoxy or $C_{1-4}$ haloalkylthio group;

$R_4$ represents a $C_{1-4}$ alkyl group;

$R_5$, $R_6$, $R_7$ independently represent a hydrogen or halogen atom or a $C_{1-4}$ alkyl, $C_{1-4}$ haloalkyl, $C_{1-4}$ haloalkoxy, $C_{1-4}$ alkylthio, $C_{1-4}$ haloalkylthio, cyano or nitro group; and $R_8$, $R_9$ independently represent a hydrogen or halogen atom or a $C_{1-4}$ alkyl group.

2. A compound as claimed in claim 1, wherein $R_3$ is chlorine, $C_{1-4}$ fluoroalkyl, $C_{1-4}$ fluoroalkoxy or $C_{1-4}$ fluoroalkylthio; $R_4$ is methyl or ethyl; and in $B_1$ and $B_2$ at least two of the substituents $R_5$ to $R_9$ are hydrogen atoms, and the remaining substituents contained in $B_1$, and $B_2$ independently represent a hydrogen, chlorine or fluorine atom or a methyl, trifluoromethyl or $C_{1-2}$-fluoroalkoxy group.

3. A compound as claimed in claim 1, wherein $R_3$ is $CF_3$, $C_2F_5$, $CHF_2O$ or $CF_3CH_2O$; $R_4$ is methyl; and B is a group of formula $B_1$':

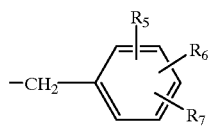
(B$_1$')

wherein $R_5$, $R_6$ and $R_7$ are independently a hydrogen or a fluorine atom and $R_5$ can further represent a methyl group;

or a group of formula $B_2'$:

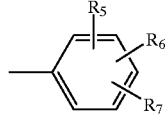
$(B_2')$

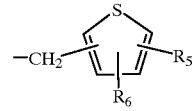
$(B_3')$ wherein $R_5$, $R_6$ and $R_7$ independently represent a hydrogen, fluorine or chlorine atom and $R_5$ can further represent a trifluoromethyl, an $OCHF_2$ or an $OCH_2CF_3$ group.

4. Compounds as claimed in claim 1 selected from the group consisting of:

- 2,6-bis(1-methyl-3-trifluoromethylpyrazol-5-yloxy)-4-methylaminopyridine;
- 2,6-bis(1-methyl-3-trifluoromethylpyrazol-5-yloxy)-4-cyanopyridine;
- 2,6-bis(2-difluoromethoxy-4-pyridyloxy)-4-methylpyridine;
- 6-(3,4-difluorobenzyloxy)-2-(1-methyl-3-trifluormethylpyrazol-5-yloxy)-4-cyanopyridine;
- 6-(4-fluorobenzyloxy)-2-(1-methyl-3-trifluoromethylpyrazol-5-yloxy)-4-cyanopyridine;
- 2-(2-difluoromethoxypyrid-4-yloxy)-6-(4-fluorobenzyloxy)-4-methylpyridine.

5. A herbicidal composition comprising a carrier, and as active ingredient a compound as claimed in claim 1.

6. A herbicidal composition according to claim 5 further comprising a surface-active compound.

7. A method for combating undesired plants, which method comprises treating a locus with a herbicidal composition as claimed in claim 5.

8. A method for combating undesired plants, which method comprises treating a locus with a herbicidally effective amount of a compound as claimed in claim 1.

9. A method for selectively combating undesired plants in maize, wheat, barley, rice and soybeans which comprises contacting said undesired plants with an effective amount of a compound as claimed in claim 1.

10. A herbicidal compound comprising a heteroaryloxypyridine of formula I:

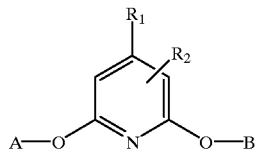
(I)

wherein

A represents independently $A_2$

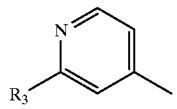
($A_2$)

B represents independently $A_2$ or one of the groups $B_1$, or $B_2$

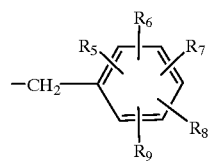
($B_1$)

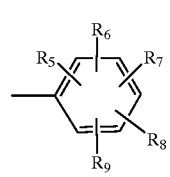
($B_2$)

$R_1$ represents a $C_{1-4}$ alkyl group;

$R_2$ represents a hydrogen or fluorine atom;

$R_3$ represents a $C_{1-4}$ haloalkoxy or $C_{1-4}$ haloalkylthio group;

$R_5$, $R_6$, $R_7$ independently represent a hydrogen or halogen atom or a $C_{1-4}$ alkyl, $C_{1-4}$ haloalkyl, $C_{1-4}$ alkoxy, $C_{1-4}$ haloalkoxy, $C_{1-4}$ alkylthio, $C_{1-4}$ haloalkylthio, cyano or nitro group; and $R_8$, $R_9$ independently represent a hydrogen or halogen atom or a $C_{1-4}$ alkyl group.

11. A compound as claimed in claim 10 wherein $R_1$ is a methyl group.

* * * * *